United States Patent [19]
McLaren et al.

[11] 3,993,493
[45] Nov. 23, 1976

[54] INKS CONTAINING ISOCYANATED IMIDES OF HYDROCARBON ANHYDRIDES AND BLENDS THEREOF

[75] Inventors: Robin A. McLaren, Ballwin; Charles Alcott, St. Louis, both of Mo.

[73] Assignee: Petrolite Corporation, St. Louis, Mo.

[22] Filed: Aug. 9, 1971

[21] Appl. No.: 170,375

Related U.S. Application Data

[62] Division of Ser. No. 788,947, Jan. 3, 1969, abandoned. Ser. No. 361,765, May 18, 1973 is a continuation of said Ser. No. 788,947.

[52] U.S. Cl. .................................. 106/20; 106/22; 106/31; 106/32; 260/28 R; 260/28.5 R
[51] Int. Cl.² ................... C09D 11/00; C09D 11/02; C09D 11/06
[58] Field of Search ............. 260/28, 28.5, 346.8 X, 260/451, 452; 106/270–272, 20–23, 31, 32, 10, 11

[56] References Cited
UNITED STATES PATENTS

| | | | |
|---|---|---|---|
| 2,486,456 | 11/1949 | Zellner | 260/452 |
| 3,030,387 | 4/1962 | Benoit | 260/28.5 X |
| 3,163,548 | 12/1964 | Stark, Jr. | 106/31 |
| 3,381,022 | 4/1968 | Le Suer | 260/404.8 |
| 3,590,076 | 6/1971 | Heintzelman et al. | 106/31 X |

*Primary Examiner*—Joan E. Welcome
*Attorney, Agent, or Firm*—Sidney B. Ring; Hyman F. Glass

[57] ABSTRACT

Reaction of (1) organic isocyanates and (2) imides of hydrocarbon-anhydrides and equivalents thereof; and to uses for these reaction products, including their use in inks, particularly in carbon paper inks.

8 Claims, No Drawings

INKS CONTAINING ISOCYANATED IMIDES OF HYDROCARBON ANHYDRIDES AND BLENDS THEREOF

This application is a Division of Copending Application Ser. No. 788,947, filed Jan. 3, 1969, now abandoned. Application Ser. No. 361,765, filed on May 18, 1973, is a Continuation of said application Ser. No. 788,947 and was copending therewith and is copending with this application Ser. No. 170,375.

This invention relates to the reaction products of (1) organic isocyanates and (2) imides of hydrocarbon-anhydrides or equivalents thereof; and to uses for these reaction products, including their use in inks, particularly in carbon paper inks.

These may be illustrated by the reaction of an organic isocyanate with the following:

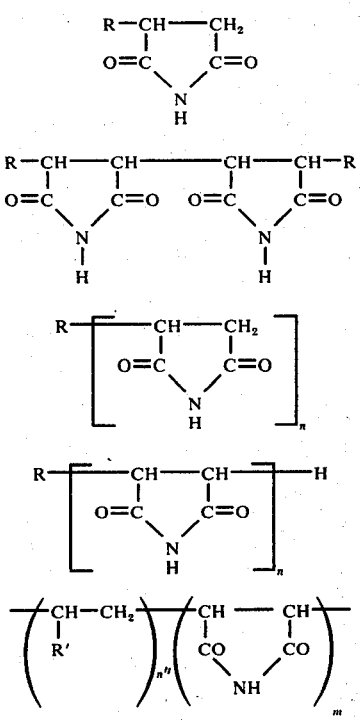

In the above formulae R is a hydrocarbon group, saturated or unsaturated, preferably a non-benzoid hydrocarbon, where R has for example at least about 12 carbons, such as from about 12 to 100 carbons, for example from about 14 to 60 carbons, but preferably from about 18 to 50 carbons and $n$ is an integer for example 1 – 5, or even 25 or more in certain instances. $R'$ is H or $(CH_2)_{n'}$ — H where $n' = 1$–100, such as 4–60, for example 6–40.

Thus, the hydrocarbon moiety may have one or more maleimide units attached thereto; said maleimide units, which may be attached to one or more positions on the hydrocarbon molecule, may be attached directly to the hydrocarbon molecular and/or to one or more other maleimide molecules. When the maleic unit is saturated it may be called a succinimide.

The term "hydrocarbon-maleimide compound" relates to the imide of the reaction of a hydrocarbon with maleic anhydride, or equivalents or derivatives thereof. It also includes derivatives of the hydrocarbon maleic reaction product. The reaction product is also referred to as a hydrocarbon succinimide.

The term "maleic compound" prior to reaction with $NH_3$ relates to maleic anhydride, maleic acid, maleic type anhydrides, esters, or acids and other derivatives thereof.

The hydrocarbon-maleic compounds of this invention may be derived from saturated hydrocarbons or unsaturated hydrocarbons in a variety of ways, for example:

1. Addition of maleic anhydride to an olefin. This reaction is also known as the "ene" synthesis (K. Alder and H. von Brachel, Annalen der Chemie, 651, 141–153 (1962)). It is illustrated by the following:

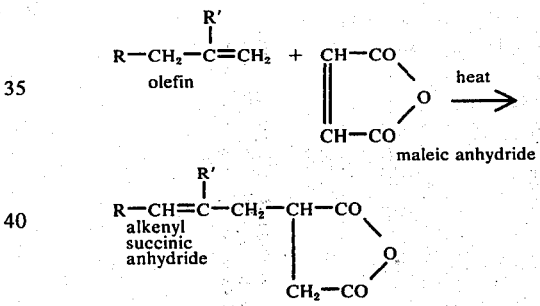

These materials are also referred to below as "maleic adducts".

2. The addition of maleic anhydride or a maleic compound to an unsaturated or saturated hydrocarbon in the presence of a free radical catalyst. It is illustrated by the following:

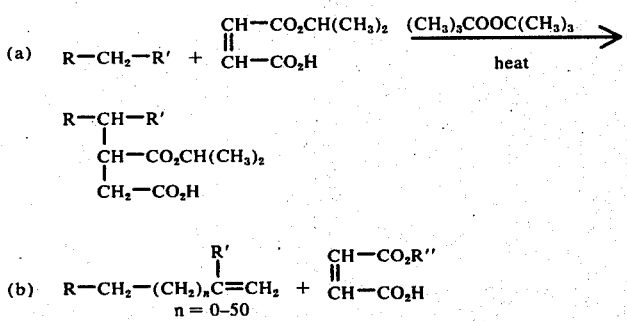

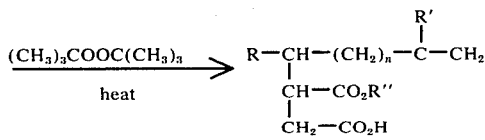

These materials are also referred to below as "maleic grafts" and have been previously described in copending application Ser. No. 527,075, filed Feb. 14, 1966, now abandoned.

In the case of (1) the olefin may be an alpha-olefin containing a terminal vinyl group or an olefin containing a vinylidene

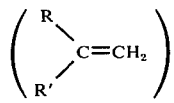

group. R may have from 9–100 or more carbons and may be straight chain or branched. R' may be hydrogen or $H(CH_2)_n$— where $n = 1$–100 or more. At present these olefins are prepared commercially by two methods (a) The thermal degradation of high molecular weight polyolefins such as polyethylene and (b) the oligomerization or polymerization of monoolefins such as ethylene. Examples of suitable olefins are dodecene, tetradecene, hexadecene, octadecene and eicosene, prepared by either method. Also higher "alpha-olefins" obtained by the polymerization of ethylene. Materials of this type currently available contain significant amounts of vinylidene as well as vinyl groups. Suitable olefins may also be prepared by the polymerization of other mono-olefins such as propylene, butene-1, isobutylene, hexene, etc. to give polymers containing vinyl or vinylidene groups which can react with maleic compounds to yield alkenyl succinic anhydride. We prefer in practice to use essentially linear olefins prepared by the polymerization of ethylene or the degradation of high molecular weight polyethylene.

In case (2) the hydrocarbon may be saturated or unsaturated. Suitable unsaturated hydrocarbons include materials suitable for case (1) plus hydrocarbons of similar structure but containing other types of unsaturation such as cis and trans unsaturation. Suitable saturated hydrocarbons are described in the above U.S. patent application Ser. No. 527,075.

The hydrocarbons may also contain minor amounts of other groups such as acids, esters, alcohols, etc.

The succinimides are prepared by reacting the hydrocarbon anhydride or its equivalent with ammonia

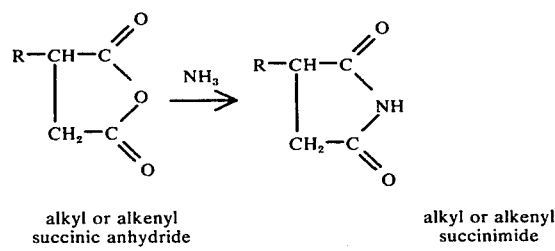

alkyl or alkenyl
succinic anhydride alkyl or alkenyl
succinimide

The use of an equivalent is illustrated with the following reaction:

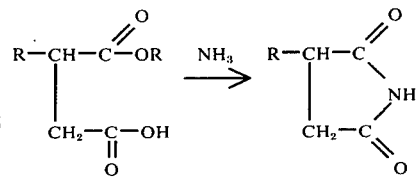

alkyl or alkenyl
succinic half-ester alkyl or alkenyl
succinimide

If a polyfunctional isocyanate is to be used it is preferred at this stage to insure substantially complete conversion to imide as the presence of diamide or amide-acid will lead to cross linking. This is further discussed below.

Because of reactivity, cost, and superior products, hydrocarbon anhydride imidified with ammonia is the preferred embodiment of this invention and will be used to illustrate the present invention.

The hydrocarbon anhydride is treated with ammonia at a temperature sufficiently high to cause reaction between the anhydride and ammonia but not so high as to decompose the hydrocarbon chain, such as temperature of at least 75°–300° C., for example 90°–200° C., but preferably from 100°–175° C.

Depending on the temperature employed, the reaction can be carried out from 30 minutes or less to 3 or more days, such as from 1 to 24 hours, but preferably from ⅔ to 12 hours. However, optimum reaction time will depend on, among other things, the temperature employed. Ammonia may be added in any satisfactory manner. In practice, imidification is generally effected by passing gaseous ammonia at the rate of at least 0.01 g./min., such as from 0.01 to 1.0 g./min., for example 0.1 to 0.5 g./min., but preferably 0.02 to 0.1 g./min., into molten hydrocarbon anhydride heated to at least about 75° C., but preferably about 100°–175° C. for a period of at least 2 hours, but more preferably 2–6 hours. Economics dictates the amount of maximum ammonia flow. Although the reaction can be carried out under superatmospheric pressure, optimum results are achieved at atmospheric pressure since superatmospheric pressure does not allow decomposition of the unstable constituents to occur as readily as effected at atmospheric pressure.

After reaction excess ammonia is removed by any suitable means, for example, gas entrainment, distillation, reduced pressure, etc. In practice, excess ammonia is removed by blowing with a gas inert with the product such as nitrogen, air, or any other suitable gas. Sufficient time is usually allowed at this stage to allow conversion of relatively minor amounts of amides to imides.

The nitrogen content of the imidified product will vary depending on the anhydride. For optimum results the nitrogen content of the final product should be a value sufficient to indicate complete imidification of all the anhydride groups present in the wax. Thus, a sufficient amount of ammonia should be added to react with at least all the carboxylic acid groups as determined by acid and saponification numbers, i.e. at least one mole of ammonia per mol-equivalent anhydride group. However, in practice an excess of ammonia is added, for example, at least one mole or more of ammonia per mol equivalent anhydride. Employing ammonia, the products in general contain at least 0.2% nitrogen, for example 0.3 to 5.0%, such as 0.5 to 3.0%, but preferably 0.5 to 2.0%, by weight.

The hydrocarbon-maleimides described herein are reacted by isocyanates to form the products of this invention. This will be illustrated with the following idealized equation:

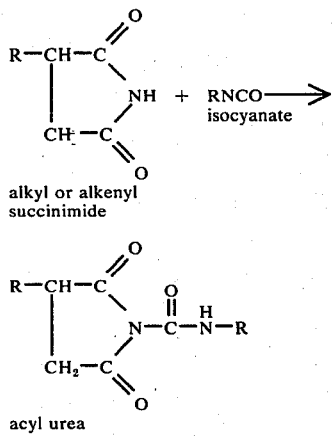

alkyl or alkenyl succinimide

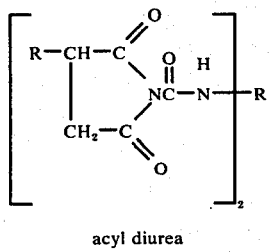

acyl urea

Where a diisocyanate R—(NCO)$_2$ is employed, the reaction product is ideally presented as $$\left[ \begin{array}{c} \text{R—CH—C} \\ | \\ \text{CH}_2\text{—C} \end{array} \begin{array}{c} \text{O} \\ \text{N—C—N} \\ \text{O} \end{array} \text{R} \right]_2$$

acyl diurea

Corresponding products are produced by reacting higher isocyanates such as triisocyanates, etc.

The preferred isocyanates of this invention are the polyisocyanates and more specifically the diisocyanates, which of course contain two distinct and separate isocyanate groups. Representative compounds are the polymethylene diisocyanates such as ethylene diisocyanate, trimethylene diisocyanate, tetramethylene diisocyanate, pentamethylene diisocyanate, etc.; the alkylene diisocyanates such as propylene-1,2-diisocyanate, butylene-1,2-diisocyanate, butylene 1,3-diisocyanate, butylene-2,3-diisocyanate; the alkylidine diisocyanates such as ethylidene diisocyanate, butylidene diisocyanate, and heptylidene diisocyanate. The cycloalkylene diisocyanates such as cyclopentylene-1,3-diisocyanate, cyclohexylene-1,2-diisocyanate, cyclohexylene-1,4-diisocyanate; the aromatic diisocyanates such as m-phenylene diisocyanate, p-phenylene diisocyanate, 1-methylphenylene-2,4-diisocyanate, 1-methylphenylene-2,6-diisocyanate, 3,3'-bitolylene-4,4'-diisocyanate, naphthylene-1,4-diisocyanate, naphthylene-1,5-diisocyanate; aliphatic-aromatic diisocyanates such as xylylene-1,4-diisocyanate, xylylene-1,3-diisocyanate, 4,4'-diphenylenemethane diisocyanate, 4,4'-diphenylenepropane diisocyanate, etc.

Substituted isocyanates can also be employed, for example, substituted derivatives of the above and other compounds containing halogens, sulfur, oxygen, etc. containing groups for example:

1-chloro-2,4-phenylene diisocyanate

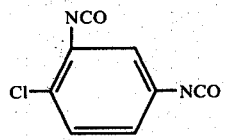

Dimethoxy-4,4'-biphenylene diisocyanate

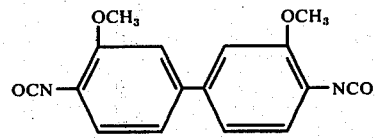

4,4'-sulfonylbis(phenyl isocyanate)

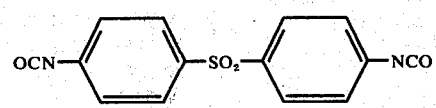

etc.

The diisocyanates of the types listed in the above paragraph are the ones which are most preferred for purposes of this invention, Examples of compounds containing more than two reactive groups of formula —N=C=O which can be used, there may be mentioned 1,2,4-benzene triisocyanate and butane-1,2,2-triisocyanate.

Of course, it should be remembered that the polyisothiocyanates may be used instead of the polyisocyanates and representative examples would be those given above with the single change that the oxygen atom is substituted by sulfur.

Especially preferred diisocyanates are commercially available diisocyanates such as those listed below.

Symbols employed in the tables and elsewhere in this application are as follows:

TABLE I

| Symbol | Name | Formula |
|--------|------|---------|
| TDI | Toluene-2,4-diisocyanate | |

TABLE I-continued

| Symbol | Name | Formula |
|---|---|---|
| TD-80 | 80% toluene-2,4-diisocyanate | (2,4-TDI structure) |
|  | 20% toluene-2,6-diisocyanate | (2,6-TDI structure) |
| MDI | Diphenylmethane-4,4'-diisocyanate | OCN—⌬—CH₂—⌬—NCO |
| NDI | Naphthylene-1,5-diisocyanate | (1,5-naphthylene diisocyanate) |
| TBDI | 3,3'-bitoluene-4,4-diisocyanate | (3,3'-dimethyl-4,4'-biphenyl diisocyanate) |
| HMDI | Hexamethylene diisocyanate | OCN(CH₂)₆NCO |
| ClPDI | 1-chloro-2,4-phenylene diisocyanate | (1-chloro-2,4-phenylene diisocyanate) |
| MBPDI | 3,3-dimethoxy-4,4'-biphenylene diisocyanate | (3,3'-dimethoxy-4,4'-biphenylene diisocyanate) |

In some cases it is also advantageous to use a monoisocyanate such as phenyl isocyanate.

In practice, from one to 20 percent of isocyanate, preferably diisocyanate, by weight of imidified anhydride is reacted with the imidified anhydride wax to give a markedly improved product. Lesser or greater amounts may also be employed for certain applications. The preferred concentration of isocyanate is from 4–12 percent.

The isocyanate may be used in an amount approximately equivalent to the imide. A slight excess is generally not detrimental and it has been found in some cases that less than an equivalent amount such as 0.5 to 0.9 equivalents may be advantageously used. Normally a catalyst is used to facilitate the imide-isocyanate reaction. Suitable catalysts are amine catalysts such as N-ethyl morpholine, triethylene diamine, triethylamine, tetramethyl-1,3-butane diamine, dimethylethethanolamine, dimethyl cyclohexylamine, N-methyldicyclohexylamine, N-cyclohexylpiperidine, and N-cyclohexylmorpholine. Organotin catalysts may also be used but we prefer in practice to use an amine catalyst.

In preparing the maleic adducts any suitable olefin may be used. The preferred types of olefins are materials of the formula R- CH=CH₂ and

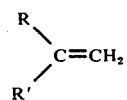

where R and R' are essentially linear hydrocarbon radicals. The total number of carbon atoms in the molecule is preferably at least 18. Especially preferred olefins are those commercially available materials known as eicosene-1, Gulf Oil Corporation $C_{22-28}$ Alpha Olefin Fraction and Gulf $C_{30+}$ Alpha Olefin Fraction. The latter two materials contain both of the above structures. Any other olefin of similar properties would also be very suitable.

Any suitable wax or wax substitute can be employed in preparing the maleic grafts. These include microcrystalline waxes, such as plastic and tank bottom derived microcrystalline waxes, solvent extracted microcrystalline waxes, etc., wax substitutes such as Fischer-Tropsch Wax, polyalkylenes such as polyethylene, polypropylene, and blends thereof, etc., such as the olefins above.

The preferred types of saturated hydrocarbon waxes employed are those having a melting point of about 150°–270° F. but preferably about 150°–220° F. and a penetration as defined by ASTM Test Method D5-25 of from about 0 + to about 50, for example 0 + to about 30, but preferably 0 + to about 10 with an optimum of 0 + to about 5. These are obtained using 100 g. total weight for 5 seconds at 77° F. Waxes found within this range are microcrystalline wax, Fischer-Tropsch wax, certain of the polyalkylenes such as polyethylenes, etc. In general, these waxes have an average of over about 40 carbons, but preferably over about 45 carbons per molecule, such as from 50–75 or 100 or more. Where the waxes are of a lower molecular weight, they should be blended with a higher molecular weight material to give this average. An especially preferred wax is Fischer-Tropsch Wax.

All of these waxes are well known. For example they are described in U.S. Pat. No. 2,890,125, which is by reference incorporated into the present application.

A unique class of polyethylenes which can be employed in this invention are those prepared by employing a catalyst which is an organolithium compound with a chelating tertiary amine, such as described for example in U.S. Pat. No. 3,206,519 and in the Journal of Organic Chemistry 29, 2928 (1964).

Another special class of polyolefins which can be employed in this invention are those prepared by the process described in U.S. Pat. No. 2,977,381.

The preferred type of olefin wax employed is that having a relatively high melting point and relatively low penetration such as the $C_{30+}$ Alpha-olefin fraction described above. Low molecular weight polyethylenes having terminal unsaturation such as those obtained as by-products in the Phillips High Molecular Weight Polyethylene Process are also suitable.

Because of its commercial importance, maleic anhydride is employed to illustrate this invention. Examples of other acids or anhydrides which may be reacted include citraconic acid, ethylmaleic acid, glutaconic acid, itaconic acid, methylitaconic acid, etc. The term "wax-maleic compound" and "maleic compound", "maleic adducts", etc., includes these acids, anhydrides and derivatives.

The maleic adducts may be prepared by heating together the olefin and maleic anhydride at at least 180°, preferably at least 200° and most preferably at least 210°. The maximum reaction temperature is dictated by the stability of the reactants and products. When a relatively impure olefin is used it may be necessary to remove high melting by-product by filtration or any other suitable method.

Although the wax-maleic grafts can be prepared by any suitable method, we have prepared these compositions by reacting wax with maleic anhydride under free radical forming conditions. In one embodiment, wax, maleic anhydride or a maleic ester and a peroxide are reacted at a temperature sufficiently high to promote free radical formation. Since heat promotes free radical formation, a temperature sufficiently high to promote the decomposition of the peroxide, without causing decomposition of reactants and products, is employed. Depending on the peroxide, temperature of about 100°–250° C., such as about 125° to 225°, for example about 150° to 215°, but preferably about 170° to 200°, are employed. The temperature should be sufficiently high to keep all reactants in solution or in a molten state.

In the case of di-tert-butyl peroxide the best yields are obtained in the ranges of about 100° to 250° C., but preferably about 170° to 200° C.

Reaction times will depend on various factors such as for example on the particular reactants, reaction conditions, etc. A reaction time sufficient to effect the desired degree of reaction completion is employed. Ordinarily, reaction times of from about 0.5 to 6 hours, such as about 0.5 to 5 hours, for example about 0.5 to 4 hours, but preferably about 1 to 3 hours are employed. Shorter or longer times may be employed to push the reaction to the desired degree of completion depending on various factors such as reactants, conditions, peroxides, etc.

Any suitable free-radical producing agent capable of forming reactive sites can be employed. These include peroxides, hydroperoxides, etc., for example benzoyl peroxide, acetyl peroxide, 2,4-dichlorobenzoyl peroxide, tert-butyl peroxide, tert-butyl hydroperoxide, methyl benzyl hydroperoxide, cumene hydroperoxide, peracetic acid, tert-butyl permaleic acid, lauryl peroxide, methyl ethyl ketone peroxide, dicumyl peroxide, di-tert-butyl diperphthalate, tert-butyl peracetate, and the like.

Other sources of free radicals besides peroxides can also be employed, for example high energy ionizing irradiation, etc., cobalt in conjunction with hydroperoxides, inorganic peroxy compounds such as persulfates, hydrogen peroxide, etc., azo compounds of the general formula r—N=N—R such as azobenzene, azomethane, azobisisobutyronitrile, etc., acyl-aryl nitrosoamides such as nitrosoanilide, etc.

The wax anhydrides can be prepared by the process described in U.S. Pat. No. 3,030,387 which is by reference incorporated into this application. This application is illustrated by Claim 9 which states:

"A process for the preparation of alkyl hydrocarbon and cycloalkyl hydrocarbon substituted succinic acid anhydrides which comprises reacting one mole of maleic anhydride with more than one mole of hydrocarbon selected from the group consisting of alkyl and cycloalkyl hydrocarbons of from 6 to 32 carbon atoms at a temperature above 100° C. and in the presence of a catalytic amount of di-tertiary-butyl peroxide."

In one embodiment maleic anhydride and the peroxide, preferably as a solution, are added to molten well-stirred wax and the reaction allowed to react to completion. The product is precipitated by pouring into a liquid in which the desired product is insoluble, and the by-products are soluble, such as methanol, and the wax separated therefrom by any suitable means such as by filtration, etc. Thereafter the product is washed with methanol and collected by filtration. The product may also be employed without further purification.

In another embodiment, the maleic half-ester is converted to the anhydride in situ.

Since acid, ester and anhydride are all converted to imide by ammonia in the present invention it is not necessary to convert the maleic graft to its anhydride form in the present case. However, such a conversion may be carried out is desired.

The following examples are presented by way of illustration and not of limitation. Examples 1–2 illustrate the preparation of maleic adducts.

EXAMPLE 1

Gulf $C_{22-28}$ Alpha-olefin (525g) was melted and 150g maleic anhydride added. The mixture was stirred at 215° for 19 hrs. to yield maleic adduct.

EXAMPLE 2

Gulf $C_{30+}$ Alpha-olefin (420g) was stirred with 100g maleic anhydride at 210° for 18 hrs. The molten product was filtered through glass-wool to yield adduct.

Examples 3–10 illustrate the preparation of maleic grafts.

EXAMPLE 3

A solution of 36 ml di-tert-butyl peroxide in 180 ml isopropyl maleate was added dropwise over a period of about 1 hr. to 1000g of Fischer-Tropsch wax. The reaction temperature was maintained at 185° C.

Examples 4–10 were prepared similarly.

| Ex. | Hydrocarbon | Wt. | Isopropyl Maleate | Di-t-butyl peroxide |
|---|---|---|---|---|
| 4 | Fischer-Tropsch Wax | 320g | 80g | 16 ml |
| 5 | Soft Microcrystalline Wax (Ultraflex) | 800g | 141g | 29 ml |
| 6 | Hard Microcrystalline Wax | 400g | 70g | 14 ml |
| 7 | $C_{30+}$ Alpha-olefin | 900g | 160g | 32 ml |
| 8 | $C_{22-28}$ Alpha-olefin | 500g | 88g | 18 ml |
| 9 | Octadecene-1 | 500g | 88g | 18 ml |
| 10 | Tetradecene-1 | 200g | 36g | 8 ml |

The maleic compound is converted to a substituted succinimide by treatment with ammonia above its melting point, preferably from 75°–175°, such as from 100°–150°. Normally a small amount of diamide (or amide-acid) remains after ammonia treatment. If a diisocyanate is to be used in the final stage cross-linking will occur leading to gelling of the final product. Thus for use in a diisocyanate reaction it is necessary to convert the diamide to imide, by any suitable method such as blowing with an inert gas or vacuum treatment. Such treatment may be optionally carried out prior to reacting a monoisocyanate. The following examples are presented for purposes of illustration and not of limitation.

EXAMPLE 11

The product of Example 1 (100g) was melted and blown with ammonia at 130° for 3 hrs. and then with nitrogen at 130° for 1 hr. to yield the imide.

The following examples were similarly prepared.

| Ex. | Product of Ex. | Wt. (gm) | $NH_3$ blowing Temp. | Time | $N_2$ blowing Temp. | Time |
|---|---|---|---|---|---|---|
| 12 | 2 | 75 | 130° | 1 hr. | 130° | 10 min. |
| 13 | 3 | 1150 | 130° | 4 hr. | 130° | 2 hr. |
| 14 | 4 | 75 | 130° | 3 hr. | 130° | 1 hr. |
| 15 | 5 | 75 | 130° | 2 hr. 40 min. | 130° | 1 hr. |
| 16 | 6 | 75 | 130° | 2 hr. | 130° | 1 hr. |
| 17 | 7 | 1050 | 130° | 3 hr. | 130° | 1 hr. |
| 18 | 8 | 330 | 130° | 2 hr. | 130° | 1 hr. 30 min. |
| 19 | 9 | 300 | 130° | 3 hr. | 130° | 3 hr. |
| 20 | 10 | 200 | 130° | 2 hr. | 130° | 4 hr. |

The reaction between the substituted succinimide and the isocyanate may be carried out with or without a catalyst. Since the uncatalyzed reaction is very slow we prefer to use a catalyst such as triethylene-diamine or N-methyl dicyclohexylamine. Any other suitable catalyst may also be used. The most preferred catalyst is N-methyl-dicyclohexylamine.

The following examples are presented for purposes of illustration and not of limitation.

EXAMPLE 21

The product of Example 11 (100g) was melted and heated to 110°, 15g tolylene diisocyanate (TD-80) added and the mixture stirred with 1g triethylenediamine for 18 hrs., maintaining the temperature at 110°. A further 1g of triethylene diamine was added and the reaction continued for a further 6½ hrs.

The following examples were similarly prepared.

| Ex. | Product of Ex. | Wt. (gm) | Isocyanate | Wt. (gm) | Total TED(a) | Total Reaction Time |
|---|---|---|---|---|---|---|
| 22 | 12 | 75 | TDI(b) | 12 | 2g | 19 hrs. |
| 23 | 13 | 100 | TDI | 9 | 2g | 18½ hrs. |
| 24 | 13 | 100 | PI(c) | 18 | 1g | 18 hrs. |
| 25 | 14 | 75 | PI | 11.5 | 1g | 17¼ hrs. |
| 26 | 15 | 75 | PI | 8.7 | 1g | 16 hrs. |
| 27 | 16 | 75 | TDI | 11 | 2g | 17 hrs. |
| 28 | 17 | 1050 | TDI | 72 | 15g | 23½ hrs. |
| 29 | 18 | 330 | TDI | 22 | 4g | 2½ hrs. |

(a)Triethylene diamine
(b)Tolylene diisocyanate (TD-80)
(c)Phenyl isocyanate

EXAMPLE 30–31

The procedure was the same as in Example 21–29 except N-methyl dicyclohexylamine was used as catalyst and was added all at the beginning of the reaction.

| Ex. | Product of Ex. | Wt. (gm) | Isocyanate | Wt. (gm) | Total TED(a) | Total Reaction Time |
|---|---|---|---|---|---|---|
| 30 | 19 | 300 | TDI | 25 | 4 | 18 hrs. |

-continued

| Ex. | Product of Ex. | Wt. (gm) | Isocyanate | Wt. (gm) | Total TED(a) | Total Reaction Time |
|---|---|---|---|---|---|---|
| 31 | 20 | 200 | TDI | 17 | 3 | 17½ hrs. |

USE IN CARBON PAPER INKS

This section deals with the utilization of the isocyanated hydrocarbon succinimides of this invention in carbon paper inks. There are several articles, patents, and other published literature which discuss various types of carbon paper, particularly in regard to formulation of the various ingredients, test procedures, utilization of various waxes, etc. See, for example, U.S. Pat. No. 2,426,248, dated Aug. 26, 1947, to Sugarman; Chapter 12 entitled "Carbon Paper and Other Duplicating Papers" by R. R. Wissinger in the book edited by R. H. Mosher entitled "Specialty Papers", published by the Chemical Publishing Co., New York in 1950; the paper on the "Rheology of Carbon Paper Inks" by E. S. Gale and B. J. Staneslow in the American Ink Maker issue of December 1950; the paper on "Converting of Carbon Papers" by F. M. McFarland in the Paper Trade Journal, Volume 137, pages 230–237 (1953); and the book Commercial Waxes by H. Bennett, pages 268, 377 and 429–431, published by Chemical Publishing Co., New York, in 1944.

There are many different types of carbon paper and related materials in use today. The three most widely used types of carbon paper are the one-time carbon which is used once and then thrown away, the pencil carbon which may also be used once, or may be used many times, and the typewriter carbon. The one-time carbon is the most widely used type of carbon paper and it finds wide application in business and multiple forms and other applications. In the production of one-time carbon paper, cost is all important. On the other hand, for typewriter carbons, quality rather than cost is important, and for pencil carbons, cost and quality are intermediate in importance.

The carbon paper ink may be viewed simply as a mixture containing a wax, an oil, a pigment and a dye. The oil serves as the vehicle and the pigment and dye give the color and some of the body. Most of the desirable characteristics in the finished ink must be supplied by the wax and these will be described later. Other materials may also be used in carbon paper to give it certain properties. For example, petrolatum may be used as part or all of the vehicle to impart certain properties such as plasticity and toughness, and paraffin wax may be used as a substitute for part of the wax to give a cheaper formulation. One of the unique properties of many of the hydrocarbon-maleic compounds of this invention is that they are able to carry a lot of paraffin wax into the ink formulation without detracting greatly from the desirable characteristics required. In this respect, these products are comparable to Carnauba and Ouricury and superior to Montan. In fact in some cases the ink may be improved by the addition of materials such as paraffin. Other materials may be used in carbon paper inks such as clay to cheapen the formula, oleic acid which acts as a dye solubilizer, rubbers to give toughness, dispersing agents, etc.

The consistency and other properties of the ink can be varied to a certain degree by the choice of the oil which is used. For example, various oils ranging from a relatively light mineral oil (100 SUS at 100° F.) up to heavy oils and petrolatums may be used. These oils and petrolatums may be colorless or range in color up to black. The darker colored materials are generally better dispersants for the pigment.

There are numerous pigments which may be used in typical formulations. The most common pigment is carbon black and this comes in numerous grades such as channel blacks, furnace blacks, etc., and each of these grades come in many modifications. The channel blacks are, in general, the most desirable as far as quality is concerned, but on the other hand, they are also the most expensive. The high-grade channel blacks have an oxygenated surface which aids in its dispersion and which can absorb the dye and other materials. As one goes down the scale of carbon blacks, lesser amounts of this very desirable oxygenated surface are encountered. Blue pigments may also be used, such as Milori Blue, and others, as can many other blue pigments. Numerous other colored pigments may also be used as described in the literature.

Many dyes are commonly employed in carbon paper inks. The common ones are Methyl Violet, Nigrosine, Victoria Blue, etc., and salts of these materials. It is advantageous to use a dye which is soluble in the wax, but if this is impossible, a solubilizer must be used. One of the advantages of using the hydrocarbon-maleic compounds of this invention is that the dye is soluble in the wax and no solubilizer is necessary. In general, any solubilizer which is used will detract from the qualities of the finished ink, i.e., will cause dye bleed, soften the ink, cause frosting, etc. In some instances it is possible to completely eliminate the dye.

A wax to be useful for this purpose, must have many specific properties when used in small concentration in the finished ink; for example, in concentrations of from 8% to 12% in one-time carbon paper inks, or in higher percentages, up to 30% or 40%, in typewriter carbons. To be useful for carbon paper inks a wax must be able to dissolve the dye, such as methyl violet, Victoria blue, nigrosine, etc., preferably without the addition of a solubilizer, such as oleic acid. In this respect, the waxes of this invention are much superior to the natural waxes Carnauba, Ouricury, and Montan which are almost universally used in one-time carbons. A wax must also produce good flow in a one-time carbon paper ink so that a thin uniform coating can be obtained. To produce good flow, a wax should give an ink of low viscosity, no thixotropy and no yield value (be newtonian). The dispersion of the carbon black and the viscosity of the wax are the important variables which influence the flow of the finished ink. The ability of a wax to disperse carbon can be measured by the procedure described by Gale and Staneslow in the aforementioned article. If a wax gives B-Type dispersion or better, at 6%, no flow difficulties would be expected. Also, in this respect, many of the products of this invention are equal to or superior to the natural waxes Ouricury, Carnauba and Montan.

Another procedure is the simple flow test described below. Many of the products of this invention are markedly superior to natural waxes on this test.

A wax must also yield a finished ink which is hard and which will not bleed oil. These properties can be easily tested, at least to a certain degree, by determining the oil retention penetration and the oil retention of a wax oil blend. In this respect, the waxes of this invention show great value and are comparable, in some cases superior, to Carnauba, Ouricury and Montan which is a property which is often so hard to duplicate.

The following are formulations employing wax-maleic compositions of this invention for a one-time carbon of medium intensity:

Carbon Paper Ink 1

| A. | Grams | Material |
|---|---|---|
| | 12 | A product of this invention (Ex. 23) |
| | 20 | Paraffin Wax (m.p. approx. 135° F.) |
| | 17 | Carbon Black |
| | 1 | Methyl Violet |
| | 50 | Mineral Oil |
| B. | Same as A except that the product of Example 27 was employed, in place of Example 23. | |

The paraffin wax used is a high-melting-point paraffin and the oil is a 100-second oil at 100° F. The carbon black can be a channel black such as exemplified by Peerless Beads or a cheaper channel black such as Raven 15, manufactured by Columbian Carbon Company, or a furnace black as exemplified by Statex B-12 manufactured by Columbian Carbon Company.

The above formulations may be modified in several ways to give different intensities and grades of ink; for example clay can be substituted for some of the carbon black and oil to cheapen the formula without greatly impairing quality, and other variations in the proportions of wax may be made.

A similar one-time carbon paper formulation employing clay is as follows:

Carbon Paper Ink 2

| A. | Grams | Material |
|---|---|---|
| | 12 | A product of this invention (Ex. 24) |
| | 25 | Paraffin Wax (m.p. approx. 135° F.) |
| | 0.5 | Methyl Violet Base |
| | 1 | Nigrosine |
| | 18 | ASP-100 clay |
| | 10 | Carbon Black |
| | 17 | 300 Sec. Mineral Oil |
| | 16.5 | Petrolatum |
| B. | The above example was repeated except that the product of Example 28 was employed, in place of Example 24. | |

One type of carbon black which may be used is a channel black such as Peerless Beads or a cheaper channel black such as Raven 15 or comparable products, or mixtures of these. These waxes also find use in other types of carbon paper and ribbons such as pencil carbons, typewriter ribbons, etc. A typical one-time medium blue pencil carbon formulation is as follows:

Carbon Paper Ink 3

| A. | Grams | Material |
|---|---|---|
| | 12 | A product of this invention (Ex. 23) |
| | 25 | Paraffin Wax (m.p. approx. 135° F.) |
| | 18 | ASP-100 clay |
| | 20 | Milori blue |
| | 13 | 300 sec. Mineral Oil |
| | 12 | Petrolatum |
| B. | The above example was repeated except that the product of Example 27 was employed, in place of Example 23. | |

A typical typewriter formulation is as follows:

Carbon Paper Ink 4

| A. | Grams | Material |
|---|---|---|
| | 25 | A product of this invention (Ex. 24) |
| | 18 | Carbon black ("Raven 15") |
| | 1 | Methyl Violet |
| | 10 | Paraffin Wax (m.p. approx. 135° F.) |
| | 16 | 300 sec. Mineral Oil |
| B. | The above example was repeated except that the product of Example 28 was employed, in place of Example 24. | |

As above, these formulations may be modified in many ways to obtain carbon paper ink to fit individual uses.

These inks may be prepared either in a ball mill or a three-roll mill by conventional procedures using temperatures of from approximately 190° F. to 220° F. Care must be taken when certain dyes are used not to exceed these temperatures; otherwise, the dye will decompose. These finished inks can be coated onto paper using a Mayer type coater or comparable equipment. Normally, it is best to apply approximately 2.5 lbs. of wax per ream for one-time carbons and higher quantities for typewriter carbons.

Among the properties which are highly desirable in carbon paper waxes are oil retention penetration and carbon dispersion. The properties are tested as follows:

Oil Retention Penetration Test

Twenty-five grams of wax on test and 25 g. of a 100 SUS mineral oil (i.e., Texaco Ink Oil No. 538) are placed in a 150 ml beaker which is covered by a watch glass and placed in an oven at 100° C. for 2 hours. Stir the sample with a glass rod, pour it into an aluminum foil dish (Fisher Scientific Company Cat. No. 8-732) resting on asbestos, and then cover with a 600 ml beaker. Allow the sample to stand for 1 hour at room temperature, then transfer to a water bath at 25.0° + or − 0.2° C. and hold for 3–4 hours. Penetration values are then obtained on the top and bottom of the sample, and these values are averaged to give the oil retention penetration. Penetration values are determined under a test load of 50 g. for 5 seconds, and are reported to the nearest tenth of a millimeter. The penetration needle employed is similar to that described in ASTM test method D 1321-54T except that the length of taper is 23 mm. rather than 6.5 mm.

The results of the above test are reported as 50/50 oil retention penetrations. The test may also be carried out using 30g oil and 20g wax. These results are reported as 60/40 oil retention penetrations.

Ink Flow Test

A test ink was prepared with the following formula:

| | Wt. % |
|---|---|
| Carnauba | 10 |
| 145 M.P. Paraffin | 12 |

-continued

| | Wt. % |
|---|---|
| 100 Sec. Ink Oil | 42 |
| Furnace Black | 20 |
| Channel Black | 10 |

The test ink is melted on a hot plate at about 225° F. and 90 parts well blended with 10 parts of the material to be tested. A drop of the mixture is allowed to fall from the end of a ⅛ inch cylindrical wood applicator on to a clean 225° F. hot plate surface. The diameter of the resulting spot is measured in cm. and reported as 10% flow. The spot size from a similar procedure using 94 parts of test ink and 6 parts of material to be tested is reported as 6% flow. A flow of 0.7 is obtained for the straight test ink.

Oil Bleed Test

An oil wax cake similar to that described under the oil retention penetration is prepared. The cake contains 60% oil and 40% wax and is approximately 4 cm. in diameter. The cake is placed on a clean 7 cm. Whatman No. 2 Filter Paper and a 150g weight placed on top of the cake. The oil bleed is reported as the percentage of the paper which is impregnated by oil after 2 hrs.

The results of the above tests on some of the materials of this invention and on two commercially available natural waxes are given in the following Table.

TABLE A

| Product of Example | Oil Retention Penetration | | Flow | | Oil Bleed |
|---|---|---|---|---|---|
| | 50/50 | 60/40 | 6% | 10% | |
| Carnauba | 15 | 28 | 0.7 | 0.7 | 0% |
| Montan | 33 | 85 | 0.7 | 0.8 | 95–98% |
| 21 | | | 1.2 | 1.4 | |
| 22 | | | 1.2 | 1.4 | |
| 23 | 52 | 106 | 0.9 | 1.2 | 25% |
| 24 | 41 | 91 | 0.9 | 1.0 | |
| 25 | | | 0.9 | 1.1 | |
| 26 | | | — | 0.8 | |
| 27 | 43 | 88 | 1.1 | 1.3 | |
| 28 | 45 | 80 | 0.8 | 1.5 | 25% |
| 29 | | | 1.0 | 1.4 | |

The data in Table A illustrate the generally good flow improving properties of the products of this invention, a property which is shown not at all by Carnauba and only to a small extent by Montan. The oil retention penetration is also satisfactory in many cases. The smaller flow improvement given by the product of Ex. 26 illustrates the preference for a fairly linear starting hydrocarbon. Good oil bleed performance is also obtained by following the teachings of this invention.

The marked flow improvement given by the waxes of this invention is remarkable and a most useful property. As mentioned above the flow of an ink is very important and use of these new waxes allows the ink formulator greater latitude in formulation. These waxes can also be used to produce new and improved carbon paper inks.

Another remarkable property of these new waxes is their behavior when blended with various other waxes. Advantageously they are blended with fairly linear hydrocarbon waxes such as high M.P paraffin, hard microcrystalline waxes, olefin waxes and Fischer-Tropsch waxes. Blends with other types of waxes which give useful properties may also be used.

Results are presented in the following Table.

TABLE B

| Product of Ex. | % | Component B | % | Component C | % | Flow 6% | Flow 10% | Oil Retention Penetration 50/50 | Oil Retention Penetration 60/40 |
|---|---|---|---|---|---|---|---|---|---|
| 28 | 100 | — | — | — | — | 0.8 | 1.5 | 45 | 80 |
| 28 | 90 | 155° M.P. Paraffin | 10 | — | — | — | 1.4 | 88 | |
| 28 | 80 | " | 20 | — | — | — | 1.4 | 44 | >100 |
| 28 | 70 | " | 30 | — | — | — | 1.4 | 35 | 99 |
| 28 | 60 | " | 40 | — | — | 1.0 | 1.6 | 35 | 48 |
| 28 | 50 | " | 50 | — | — | 0.9 | 1.4 | 30 | 50 |
| 28 | 40 | " | 60 | — | — | — | 1.0 | 58 | — |
| 28 | 30 | " | 70 | — | — | — | 1.2 | 72 | — |
| 28 | 60 | " | 20 | Fischer-Tropsch Wax | 20 | 0.9 | 1.4 | 37 | 85 |
| 28 | 90 | — | — | " | 10 | — | 1.6 | 70 | — |
| 28 | 70 | — | — | " | 30 | — | 1.4 | 45 | — |
| 28 | 50 | — | — | " | 50 | 1.4 | 45 | — | — |
| 28 | 80 | $C_{30}$ α ± olefin | 20 | — | — | — | 1.6 | 78 | — |
| 28 | 70 | " | 30 | — | — | — | 1.5 | 67 | — |
| 28 | 60 | " | 40 | — | — | — | 1.6 | 67 | — |
| 23 | 100 | — | — | — | — | 0.9 | 1.2 | 52 | 106 |
| 23 | 80 | 155° M.P. Paraffin | 20 | — | — | — | 1.4 | 31 | — |

It is not surprising to find that the addition of 10% of other waxes to the product of Ex. 28 is detrimental, but it is very remarkable that the addition of further amounts of the other wax then gives an improved product. The same behavior is seen with the product of Ex. 23. The properties continue to improve until an optimum is reached at about 40–50% other wax. It is surprising that in at least two cases the blend is superior in oil retention to Ex. 28 product. A further remarkable fact is that 6% Ex. 28 product blended with 4% paraffin gives much better flow than 6% added alone.

USE IN OTHER INKS

Some of the products of this invention are also useful in other types of inks such as liquid inks. Examples of such inks are news ink, flexographic ink, rotogravure ink and screen ink.

The product of Ex. 29 was tested in a typical news ink formula and compared with two flow improving additives used commercially. A control ink was prepared containing

| | |
|---|---|
| 100 sec. Mineral Oil | 450 parts |

-continued

| Carbon Black | 50 parts |
|---|---|

Test inks were prepared in which 5 and 10 parts respectively of the oil were replaced by 5 and 10 parts of the additives to be tested. These inks are referred to as "1% additive ink" and "2% additive ink" respectively. The inks were tested for Jetness, Viscosity, Flow and Fineness by standard methods. The results are shown in the following Table.

TABLE C

| Additive | Jetness | | Viscosity (Stormer) | | Flow (Brass Slide) | | PC Fineness | |
|---|---|---|---|---|---|---|---|---|
| | 1% | 2% | 1% | 2% | 1% | 2% | 1% | 2% |
| None | 1 | 1 | 76 | 76 | 0 | 0 | 5+ | 5+ |
| "Coblax 1000" | 1 | 2 | 63 | 60 | 46 | 74 | 5+ | 6− |
| Gilsonite | 2 | 2¼ | 57 | 59 | 88 | 87 | 6+ | 5+ |
| Prod. of Ex. 29 | 1¼ | 3 | 61 | 57 | 62 | 100 | 6− | 6 |

The results indicate the product of Ex. 29 to be superior to one of the commercial additives and about equal to the other. The products of Examples 30 and 31 are also useful as additives for liquid inks.

OTHER USES

The products of this invention are also useful in other systems where carbon black is present in an organic medium. Examples of such systems are black rubber goods, black-loaded plastics e.g. polyethylene, PVC and ABS, paints containing carbon black or pigments which interact with the products of this invention.

Having thus described our invention what we claim as new and desire to obtain by Letters Patent is:

1. A carbon paper ink containing a coloring material, a vehicle and the reaction product of
1. an organic isocyanate or a mixture of organic isocyanates and
2. an imide of a member selected from the group consisting of i. an olefin-maleic compound adduct prepared by reacting (a) a maleic compound selected from the group consisting of maleic acid, citraconic acid, ethylmaleic acid, glutaconic acid, itaconic acid, methylitaconic acid the anhydride of each of said acids and an ester derivative of each of said acids with (b) an olefin of the formula $R-CH=CH_2$ or of the formula

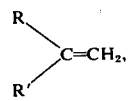

where R is a hydrocarbon radical of 9–100 carbon atoms and R' is hydrogen or $H(CH_2)_n$, $n$ being 1–100, and ii. a wax-maleic compound graft copolymer prepared by reacting (a) a maleic compound selected from the group consisting of maleic acid, a citraconic acid, ethylmaleic acid, glutaconic acid, itaconic acid, methylitaconic acid, the anhydride of each of said acids and an ester derivative of each of said acids with (b) a wax selected from the group consisting of plastic microcrystalline waxes, tank bottom microcrystalline waxes, solvent extracted microcrystalline waxes, Fischer-Tropsch waxes, polyalkylene hydrocarbon waxes and blends thereof.

2. The carbon paper ink of claim 1 wherein (1) is an organic isocyanate or a mixture of organic diisocyanates.

3. The carbon paper ink of claim 2 wherein (2) is an imide of an olefin-maleic compound adduct.

4. The carbon paper ink of claim 2 wherein (2) is an imide of a wax-maleic compound graft copolymer.

5. The carbon paper ink of claim 4 wherein (1) is a mixture of toluene diisocyanates.

6. The carbon paper ink of claim 5 wherein said mixture of toluene diisocyanates is 80% toluene-2,4-diisocyanate and 20% toluene-2,6-diisocyanate.

7. The carbon paper ink of claim 2 wherein (1) is an organic isocyanate.

8. The carbon paper ink of claim 7 wherein said organic isocyanate is phenyl isocyanate.

* * * * *